US010596104B2

(12) United States Patent
Stefani

(10) Patent No.: US 10,596,104 B2
(45) Date of Patent: Mar. 24, 2020

(54) METHOD FOR PRODUCING A TISSUE PAPER SHEET MATERIAL CONTAINING AN ADJUVANT SUBSTANCE FOR THE TREATMENT OF ALLERGIC RHINITIS, AND THE PRODUCT OBTAINED

(71) Applicant: DELICARTA S.P.A., Porcari (IT)

(72) Inventor: Emi Stefani, Porcari (IT)

(73) Assignee: SOFIDEL S.P.A., Porcari (LU) (IT)

( * ) Notice: Subject to any disclaimer, the term of this patent is extended or adjusted under 35 U.S.C. 154(b) by 0 days.

(21) Appl. No.: 14/326,779

(22) Filed: Jul. 9, 2014

(65) Prior Publication Data

US 2015/0017224 A1 Jan. 15, 2015

(30) Foreign Application Priority Data

Jul. 10, 2013 (IT) ................................ FI2013A0167

(51) Int. Cl.

| | |
|---|---|
| ***A61K 9/00*** | (2006.01) |
| ***A61K 9/50*** | (2006.01) |
| ***A61K 9/48*** | (2006.01) |
| ***A61K 9/70*** | (2006.01) |
| ***A61K 9/51*** | (2006.01) |
| ***A61K 36/28*** | (2006.01) |
| ***A61K 36/282*** | (2006.01) |
| ***D21H 17/02*** | (2006.01) |
| ***D21H 27/00*** | (2006.01) |
| ***D21H 21/36*** | (2006.01) |
| ***D21H 21/54*** | (2006.01) |
| ***D21H 17/03*** | (2006.01) |
| ***A61K 36/15*** | (2006.01) |
| ***A61K 36/53*** | (2006.01) |
| ***A61K 36/9068*** | (2006.01) |
| ***A61K 47/10*** | (2017.01) |
| ***A61K 47/14*** | (2017.01) |
| ***D21H 17/52*** | (2006.01) |
| ***D21H 17/53*** | (2006.01) |
| ***D21H 17/59*** | (2006.01) |

(52) U.S. Cl.

CPC ............ *A61K 9/0043* (2013.01); *A61K 36/15* (2013.01); *A61K 36/28* (2013.01); *A61K 36/282* (2013.01); *A61K 36/53* (2013.01); *A61K 36/9068* (2013.01); *A61K 47/10* (2013.01); *A61K 47/14* (2013.01); *D21H 17/02* (2013.01); *D21H 17/03* (2013.01); *D21H 17/52* (2013.01); *D21H 17/53* (2013.01); *D21H 17/59* (2013.01); *D21H 21/36* (2013.01); *D21H 21/54* (2013.01); *D21H 27/002* (2013.01)

(58) Field of Classification Search

None

See application file for complete search history.

(56) References Cited

U.S. PATENT DOCUMENTS

| | | | | |
|---|---|---|---|---|
| 3,686,025 | A * | 8/1972 | Morton | 510/520 |
| 5,840,403 | A * | 11/1998 | Trokhan | D21H 21/14<br>162/113 |
| 6,984,617 | B2 * | 1/2006 | Holland et al. | 510/441 |
| 2003/0232730 | A1 * | 12/2003 | Holland | A61K 8/11<br>510/101 |
| 2005/0175651 | A1 * | 8/2005 | Simonnet | A61K 9/5146<br>424/401 |
| 2006/0248665 | A1 * | 11/2006 | Pluyter | A61K 8/11<br>8/406 |
| 2008/0115898 | A1 * | 5/2008 | Gelli | B31F 1/07<br>162/109 |
| 2008/0223535 | A1 * | 9/2008 | Eichhorn | C11D 1/83<br>162/123 |

FOREIGN PATENT DOCUMENTS

| | | | |
|---|---|---|---|
| DE | 4000920 | A1 | 7/1991 |
| EP | 2213588 | A1 | 8/2010 |
| WO | 02/081819 | A1 | 10/2002 |

OTHER PUBLICATIONS

A webpage from www.thegoodscentscompany.com, [retrieved on Sep. 20, 2016]. Retrieved from the Internet: <URL:http://www.thegoodscentscompany.com/data/rw1367001.html>.*

* cited by examiner

*Primary Examiner* — David J Blanchard
*Assistant Examiner* — John P Nguyen
(74) *Attorney, Agent, or Firm* — McGlew and Tuttle, P.C.

(57) ABSTRACT

The following steps are provided for producing a sheet cellulose material, for instance a handkerchief, comprising at least one adjuvant substance for the treatment of allergic rhinitis:

generating an aqueous nano- or micro-emulsion containing nano- or micro-droplet of said at least one substance encapsulated in a protective layer comprising a non-ionic surface-active agent;

applying the nano- or micro-emulsion to the cellulose material;

evaporating water, leading to the formation of nano- or micro-capsules anchored to the cellulose fibers.

25 Claims, No Drawings

METHOD FOR PRODUCING A TISSUE PAPER SHEET MATERIAL CONTAINING AN ADJUVANT SUBSTANCE FOR THE TREATMENT OF ALLERGIC RHINITIS, AND THE PRODUCT OBTAINED

TECHNICAL FIELD

The present invention relates to improvements to cellulose products, especially paper products, particularly tissue paper products, in particular for example handkerchiefs made of tissue paper or the like, and to methods of manufacturing.

STATE OF THE ART

In the field of the production of paper products, in particular tissue paper, disposable products are often manufactured, which have particular features, according to their final purpose, usually making their use more pleasant and therefore increasing the sales thereof.

Typically handkerchiefs with different fragrances are for example produced. In some cases tissue paper products are produced, soaked with cleansing substances, for face cleaning, make-up removal or for similar uses. These products are usually singularly packaged in sealed envelopes to prevent evaporation of the cleansing substances.

Other products of this type are soaked with disinfectant substances and are sold singularly sealed, again to prevent evaporation of the disinfectant liquid and to avoid contamination of the product destined to medication.

According to EP-A-2213588, an adjuvant substance of plant origin for the treatment of allergic rhinitis is applied to a tissue paper, especially a handkerchief. In some embodiments disclosed in EP-A-2213588, the active ingredient is encapsulated into microcapsules that are then made adhere to the cellulose structure. This publication does not describe specific methods for producing the microcapsules.

WO-A-02/081819 discloses a softening composition for cellulose fibers containing amino-silicone. In some embodiments the used microcapsules may also contain perfumes, E vitamin and other substances. The microcapsules are big, in the order of some tens if micrometers. Some methods are generically described for applying the microcapsules, for instance by means of an aqueous suspension of glue, to bond them to the fibers. Neither oils nor other adjuvant substances for the treatment of allergic rhinitis are disclosed.

In DE-A-4000920 microcapsules are used in the order of 500 micrometers, anchored to the fibers forming a handkerchief or the like, for instance by means of glues. The microcapsules have a solid wall that, due to its particular conformation, is broken when the handkerchief is used.

DESCRIPTION OF THE INVENTION

The invention discloses an innovative method for combining one or more substances for the treatment of allergic rhinitis and a paper product, preferably a tissue paper product, for instance a paper handkerchief, or other cellulose product in web or sheet material.

A method is especially disclosed, allowing to produce microcapsules that are highly stable for a long time, to protect the encapsulated substances against light and atmospheric agents, and facilitating the substance absorption while using the cellulose product.

According to a further aspect, a method is disclosed allowing to apply, in a particularly efficient way, substances for the treatment of allergic rhinitis during the step of producing or preferably during the step of converting the tissue paper or other cellulose fibers-based material, with which the finished product is manufactured.

In an embodiment the adjuvant substance for the treatment of allergic rhinitis is an essential oil. It is also particularly advantageous, and represents therefore an improvement of the invention, the use of a mixture containing two or more essential oils, at least one of which is an adjuvant for the treatment of allergic rhinitis. Examples of essential oils and mixtures thereof that can be used will be detailed below.

Before being applied on the cellulose sheet that will form the finished product, the adjuvant substance for the treatment of allergic rhinitis, for instance an essential oil or a mixture containing two or more essential oils, is advantageously encapsulated in micrometric or sub-micrometric particles, also called micro- or nano-particles.

The term micro-particles or nano-particles is generally used for two different systems: micro- or nano-spheres, comprised of a porous polymer shell, inside which the active ingredient is absorbed; micro- or nano-capsules with a "core-envelope" vesicular structure, wherein the core is composed of a lipophilic active ingredient and the envelope or outer protective layer is a surface-active agent protecting the core. In this invention the second system is used, i.e. the production of vesicular micro- or nano-particles, also called herein micro- or nano-capsules.

According to the prior art, the vesicular systems may be prepared by partially or totally removing water from aqueous micro- or nano-emulsions. According to an aspect of the invention, these emulsions are prepared by means of the phase-reversal method; however, it is also possible to use different techniques, for instance those described by M YU Koroleva et al: "Nanoemulsions: the properties, methods of preparation and promising applications"; in Russian Chemical Reviews 81(1) 21-42 (2012, The Russian Academy of Sciences and Turpion Ltd, whose content is incorporated herein by reference.

According to an embodiment the invention, for preparing the nano-emulsion, a first step is provided, of preliminary preparing a mixture of one or more adjuvant substances for the treatment of allergic rhinitis, for instance and preferably one or more essential oils, at least one of which is an adjuvant for the treatment of allergic rhinitis, and a suitable non-ionic surface-active agent, up to producing a homogeneous solution. In some embodiments, in case a mixture of more essential oils is used, a first step of mixing these essential oils up to produce a homogeneous mixture and a subsequent step of mixing this mixture in the non-ionic surface-active agent may be provided.

As it will be better explained herein, the non-ionic surface-active agent forms on the finished product a lipid membrane protecting the adjuvant substance(s) for the treatment of allergic rhinitis and constituting the outer part or envelope of micro- or mini-capsules adhering to the fiber structure of the cellulose material.

In some embodiments the ratio of non-ionic surface-active agent to essential oil or mixture of essential oils, or any other adjuvant substance(s) for the treatment of allergic rhinitis is comprised preferably between 10:1 and 1:1.

According to some embodiments, the non-ionic surface-active agent has a molecular weight greater than 400, comprised for instance between 400 and 3000.

In advantageous embodiments, the non-ionic surface-active agent may be chosen from the group comprising: block or random copolymers of ethylene oxide and propylene oxide; siloxane-polyoxyalkylenes; polyethyleneglycol esters of partially or fully hydrogenated castor oil; esters of fatty acids of sorbitan; polyethoxylated of fatty alcohols; monoesters of fatty acids of glycerol; esters of fatty acids of polyethyleneglycol; or combinations thereof.

According to an embodiment, to produce micro- or nano-capsules containing the essential oils and to facilitate the application of the vesicular micro-capsules to the fiber structure of the tissue paper sheet, in a second step of the process an aqueous solution containing a cationic surface-active agent is added to the mixture of non-ionic surface-active agent and essential oil(s) or other adjuvant substances for the treatment of allergic rhinitis. Due to the phase reversal, a micro- or nano-emulsion of the essential oils or other adjuvant substances for the treatment of allergic rhinitis is formed, having an outer layer comprised of a non-ionic surface-active agent, in aqueous suspension.

The aqueous nano-emulsion produced can be applied to the cellulose structure of the tissue paper sheet.

Generally, the non-ionic surface-active agent has a lipophilic part and an hydrophilic part. Diluting the mixture of non-ionic surface-active agent and essential oils in the aqueous solution of cationic surface-active agent, the non-ionic surface-active agent forms micro-capsules or nano-capsules containing the oils or the mixture of oils. In micro-emulsions, the micro-droplets formed in the aqueous suspension have a generally round shape and may have for instance a dimension (diameter) equal to or lower than 100 micrometers, preferably equal to or lower than 50 micrometers, more preferably equal to or lower than 10 micrometers, for instance equal to or lower than 5 micrometers. In other embodiments nano-emulsions may be formed. Reference is generally made to nano-emulsions when the droplets have a diameter lower than 1000 nanometers (i.e. lower than a micrometer). Especially, the nano-droplets typically have a diameter equal to or lower than 100 nanometers.

According to some embodiments of the invention, the percentage by weight of cationic surface-active agent in the final emulsion (micro- or nano-emulsion) is comprised between 1% and 40%. In some preferred embodiments, the cationic surface-active agent is comprised between 10% and 30% b y weight of the total emulsion, and more preferably between 15% and 20% by weight. All intermediate values and all sub-ranges comprised in the ranges indicated above fall within the scope of the present disclosure.

In some embodiments the cationic surface-active agent may be selected from the group comprising: dialkyl dimethyl ammonium chlorides having C8 to C30 alkyl groups; diethyl ester dimethyl ammonium chlorides wherein ester is derived from a fatty acid; 1-3-dialkyl-2-methylimidazole chlorides having C6 to C30 alkyl groups; and combinations thereof.

Practically, the cationic surface-active agent functions as a softener for the cellulose fiber and, as it will be better described below, as a carrier for applying the micro- or nano-capsules containing the essential oil(s), or other adjuvant substance or the treatment of allergic rhinitis, to the structure formed by the cellulose fiber of the paper product.

Substantially, in the produced emulsion there are vesicular micro- or nano-capsules, i.e. micro- or nano-droplets containing one or more essential oils and externally delimited by a part or envelope formed by the non-ionic surface active agent in aqueous suspension. The cationic surface-active agent may interact with the envelope surface, thus stabilizing the vesicular system, i.e. the micro- or nano-droplets. From an experimental viewpoint it should be noted that, mixing only the mixture of essential oils and the cationic surface-active agent, the oils are not solubilized (the oil droplets are still visible to the naked eye). The same occurs when the solution of non-ionic surface-active agent+oils mixture is diluted in water. The oils are not solubilized also if the non-ionic surface-active agent is firstly mixed with the cationic surface-active agent solution and then the oil mixture is added. This shows that, by providing an initial step of mixing the essential oil(s) with non-ionic surface-active agent and a subsequent step of diluting with an aqueous solution of cationic surface-active agent, these two surface-active agents have a booster effect in stabilizing the nano-emulsion, and this means that the cationic surface-active agent co-acts with the non-ionic surface-active agent forming the envelope of the micro- or nano-droplets.

In some embodiments the water is comprised between 60% and 90% by weight of the emulsion thus obtained. All intermediate values and all sub-ranges comprised in the range indicated above fall within the scope of the disclosure.

A volatile non-aqueous solvent may also be added to the emulsion described above. This volatile non-aqueous solvent may be added for instance in a percentage comprised between 5% and 15% by weight of the total emulsion. All intermediate values and all sub-ranges comprised in the range indicated above fall within the scope of the disclosure.

The quantity of essential oil or mixture of essential oils in the emulsion is preferably comprised between 0.1% and 5% by weight, preferably between 0.5% and 3% by weight, for instance between 0.6% and 1.5% b y weight. All inter mediate values and all sub-ranges comprised in the ranges indicated above fall within the scope of the disclosure.

The nano- or micro-emulsion produced can be applied to the cellulose material using any technique for distributing the emulsion on the cellulose material in a sufficiently uniform manner. In some embodiments the emulsion may be atomized or sprayed onto the cellulose material.in the form of ply.

In other embodiment, the emulsion is applied by means of a lotion applicator. In this case the ply or sheet cellulose material may be fed along a path where an applicator is arranged, for instance an application roller, on the surface of which a layer of emulsion is distributed. The application roller may be for instance immersed in a tank, or it may be in contact with a second distribution roller taking emulsion from the tank and distributing it on the surface of the application roller. The application roller surface may have a surface finishing, for instance an engraving, a net or the like, to retain the emulsion and distribute it on the cellulose material driven around the application roller, along an arc of contact, defined for instance by a pair of guiding rollers.

The nano- or micro-emulsion containing the nano- or micro-droplets in aqueous suspension is applied on the cellulose material in quantities comprised for instance between 0.5% and 20%, preferably between 1% and 10%, more preferably between 1% and 10%, and in particular between 2% and 5% by weight with reference to the weight of the cellulose material. All intermediate values and all sub-ranges comprised in the ranges indicated above fall within the scope of the disclosure.

The cellulose material may be a sheet or web material, and may comprise one ply or more plies, i.e. a multi-ply web or sheet material for instance formed by two, three, four or more cellulose plies. The cellulose plies may be bonded to one another, for instance by means of embossing, mechanical ply-bonding, gluing or combinations thereof, for instance before, during or even after the application of the micro- or nano-emulsion.

In some embodiments the finished product (for instance a handkerchief) is produced by unwinding a continuous cellulose web material wound in multi-ply reels, i.e. reels formed by two or more plies, previously wound on the reel. In this case the nano- or micro-emulsion (i.e. the aqueous solution of cationic surface-active agent with suspension of nano- or micro-droplets with a lipid membrane formed by the non-ionic surface-active agent containing the essential oils) is applied by spraying or by means of a lotion applicator, or in any other way, on the multi-ply web material. In some embodiments the emulsion is applied on both faces of the web material, resulting in a more effective distribution of the nano- or micro-capsules.

The solution of nano- or micro-capsules may be applied on one or both the faces of a single ply; also, if necessary, two or more plies may be combined together, nano- or micro-capsules containing essential oils having been applied to at least one face or both faces of one or more than one of these plies.

In some embodiments the finished product grammage, i.e. the weight per surface unit of the cellulose material, is comprised between 30 and 1 00 g/$m^2$. In preferred embodiments, the weight per surface unit is comprised between 40 and 80 g/$m^2$, more preferably between 40 and 70 g/$m^2$ for instance between 50 and 65 g/$m^2$.

Independently of the technique used for distributing the nano- or micro-emulsion, during application the water of the aqueous solution evaporates at least partially, while the cationic surface-active agent adheres to the cellulose fibers, forming anchoring points where the micro- or nano-capsules are anchored to the fibers. The positively charged ends of the molecules of cationic surface-active agent are anchored to the fibers, whose surface is negatively charged. In this way it is possible to avoid or reduce the tendency of the micro- or nano-capsules to penetrate the fiber porous structure, so that the most part of the micro- or nano-capsules remains on the outer surface of the cellulose fibers.

In the subsequent cellulose-material converting steps it is possible to provide for the complete water evaporation so that only vesicular micro- or nano-capsules remain in the structure of the cellulose material, anchored by means of the cationic surface-active agent to the fiber structure of the same cellulose material. Any non-aqueous solvent in the solution applied to the cellulose material is also caused to evaporate.

In some embodiments the micro- or nano-capsules may comprise an essential oil selected from the group comprising: *Cardiospermum Halicacabum* essential oil; essential oil extracted from *Echium Plantagineum* seeds; *Melaleuca Alternifolia* essential oil; Ginger essential oil; *Eugenia Caryophyllata* essential oil; *Cupressus Sempervirens* essential oil; *Origanum Majorana* essential oil; *Pinus Sylvestris* essential oil; essential oil extracted from *Helianthus Annuus* seeds; *Hyssopus officinalis* essential oil; *Artemisia* essential oil; Melissa essential oil; and combinations thereof.

In a preferred embodiment a mixture of two essential oils, chosen from the group defined above, is used. In fact, it has been surprisingly discovered that the combination of two oils gives a synergy effect in terms of effectiveness of the symptomatic and therapeutic treatment of allergic rhinitis, significantly greater than the effect of the two oils separately. In a particularly advantageous embodiment, a mixture is used of the following: *Echium Plantagineum* seed extract; *Cardiospermum Halicacabum* essential oil; *Helianthus Annuus* seed cold extract, in particular oils that cannot be saponified; adding, if necessary, a homogenizing agent, for instance octyldodecanol.

A paper handkerchief, to which the emulsion described above has been applied, is innovative with respect to the currently marketed products, as it allows people suffering from allergic rhinitis to benefit from the use of this handkerchief: the adjuvant substance is not absorbed inside the cellulose support, but rather remains available for being transferred onto the skin surface during normal use of the handkerchief. Moreover, the use of vesicular systems allows a better protection for the oils mixture, protecting it against degradation, for instance oxidation or light exposure.

Furthermore, the non-ionic surface-active agent forming the envelope of the vesicles constituting the micro-capsules helps the essential oils in being absorbed by the skin, once these oils have been released due to the dissipation of the containing structure resulting from the mechanical friction between cellulose structure and skin.

Other products, substances or elements having complementary or simply additional functions may also be applied onto the handkerchief in liquid, solid (for instance powder), micro-encapsulated, nano-encapsulated form or any other adequate form. For example scented, cleansing, emollient substances or others can be used.

The invention can be based upon the use of one or more of the essential oils of the above mentioned plants, but it is also possible to use essential oils of other nature, or also substances other than the essential oil, but provided with adjuvant effects in the treatment of allergic rhinitis.

As mentioned above, the micro- or nano-capsules of essential oils or other adjuvant substances for the treatment of allergic rhinitis are preferably applied on the cellulose support, with which the handkerchiefs or other cellulose products are then produced, in an intermediate step of the converting cycle, between the unwinder of a tissue paper reel and the folding machine forming the handkerchiefs. In other embodiments the micro-capsules may also be applied, by means of a lotion applicator or in any other way, in a previous step, for instance between an unwinder and a rewinding machine. In further embodiments the micro- or nano-capsules of adjuvant substances for the treatment of allergic rhinitis may be applied after the cellulose ply formation, for instance downstream of a Yankee dryer, a drying roller or other drying device generally used in a continuous machine before forming a parent reel. The application of the micro-capsules during the final converting step, before cutting and folding (for instance in the case of folded handkerchiefs) has the advantage of reducing thermal and mechanical stresses to which micro-capsules are subjected between the application thereof and the final packaging of the finished product.

In other embodiments the handkerchief can be obtained by means of a of a dry forming system (so called air-laid technique). In this case the mixture of micro-encapsulated or nano-encapsulated essential oils can b e applied more easily on the ply being formed, as this occurs without the presence of the large amount of water, which characterizes the wet-processes of paper manufacturing. The micro-encapsulated material can be put into suspension in the air current transporting the fibers. In other embodiments the micro-encapsulated material can be applied directly on the ply in the step of formation on the fabric, or in a subsequent step.

What is claimed is:

1. A method for producing a cellulose sheet material, the method comprising the steps of:

forming a mixture consisting of at least one adjuvant substance for the treatment of allergic rhinitis with at least one non-ionic surface-active agent;

mixing the mixture of the at least one non-ionic surface-active agent and the at least one adjuvant substance for the treatment of allergic rhinitis in an aqueous solution of a cationic surface-active agent forming thereby an aqueous nano- or micro-emulsion containing nano- or micro-droplet of the at least one adjuvant substance encapsulated in a protective layer comprising the least one non-ionic surface-active agent, the cationic surface-active agent co-acting with the at least one non-ionic surface-active agent in forming an envelope of said nano- or micro- droplets, the envelope being formed while mixing the mixture of the at least one non-ionic surface-active agent and the at least one adjuvant substance with the aqueous solution of the cationic surface-active agent, wherein the envelope is formed by the cationic agent and the at least one non-ionic surface-active agent, the cationic surface-active agent stabilizing the envelope protecting a core containing the at least one adjuvant substance, wherein the cationic surface-active agent and the at least one non-ionic surface-active agent are in contact with each other prior to formation of the envelope;

applying said nano- or micro-emulsion to the cellulose material having a cellulose fiber-based structure; and evaporating water, leading to the formation of nano- or micro-capsules anchored to the fiber-based structure of the cellulose sheet material.

2. The method according to claim 1, wherein said at least one adjuvant substance for the treatment of allergic rhinitis is a substance of plant origin, said at least one adjuvant substance comprising an essential oil.

3. The method according to claim 1, wherein said at least one adjuvant substance for the treatment of allergic rhinitis comprises at least two essential oils, at least one of which is an adjuvant for the treatment of allergic rhinitis.

4. The method according to claim 1, wherein the at least one adjuvant substance for the treatment of allergic rhinitis contains at least one essential oil selected from the group comprising: *Cardiospermum Halicacabum* essential oil, *Echium Plantagineum* seed extract, *Melaleuca Alternifolia* essential oil, Ginger essential oil, *Eugenia Caryophyllata* essential oil, *Cupressus Sempervirens* essential oil, *Origanum Majorana* essential oil, *Pinus Sylvestris* essential oil, *Helianthus Annuus* seed cold extract, *Hyssopus officinalis* essential oil, *Artemisia* essential oil, *Melissa* essential oil.

5. The method according to claim 1, wherein the at least one non-ionic surface-active agent is a surface-active agent with a lipophilic part, wherein the envelope is formed in a manufacturing step which starts when no envelope exists.

6. The method according to claim 1, wherein said at least one non-ionic surface-active agent has a molecular weight equal to or greater than 400.

7. The method according to claim 1, wherein said at least one non-ionic surface-active agent is selected from the comprising: block or random copolymers of ethylene oxide and propylene oxide; siloxane-polyoxyalkylenes; polyethyleneglycol esters of partially or fully hydrogenated castor oil; esters of fatty acids of sorbitan; polyethoxylated of fatty alcohols; monoesters of fatty acids of glycerol; esters of fatty acids of polyethyleneglycol; or combinations thereof.

8. The method according to claim 1, wherein said cationic surface-active agent is selected from the group comprising: dialkyl dimethyl ammonium chlorides having C8 to C30 alkyl groups; diethyl ester dimethyl ammonium chlorides wherein ester is derived from a fatty acid; 1-3-dialkyl-2-methylimidazole chlorides having C6 to C30 alkyl groups; and combinations thereof.

9. The method according to claim 1, wherein said nano- or micro-emulsion is applied on the cellulose material in quantities comprised between 0.5% and 20% by weight with reference to the weight of the cellulose material.

10. The method according to claim 1, wherein said cellulose material has a weight per surface unit comprised between 30 and 100 $g/m^2$.

11. The method according to claim 1, wherein said micro-capsules have a diameter equal to or lower than 100 micrometers.

12. The method according to claim 1, wherein said micro- or nano-capsules have a diameter equal to or lower than 1 micrometer.

13. The method according to claim 1, wherein said non-ionic surface-active agent has a molecular weight comprised between 400 and 3000.

14. The method according to claim 1, wherein said nano- or micro-emulsion is applied on the cellulose material in quantities comprised between 1% and 10% by weight with reference to the weight of the cellulose material.

15. The method according to claim 1, wherein said nano- or micro-emulsion is applied on the cellulose material in quantities comprised between 2% and 5% by weight with reference to the weight of the cellulose material.

16. The method according to claim 1, wherein said cellulose material has a weight per surface unit comprised between 40 and 80 $g/m^2$.

17. The method according to claim 1, wherein said cellulose material has a weight per surface unit comprised between 40 and 70 $g/m^2$.

18. The method according to claim 1, wherein said cellulose material has a weight per surface unit comprised between 50 and 65 $g/m^2$.

19. The method according to claim 1, wherein said micro-capsules have a diameter equal to or less than 50 micrometers.

20. The method according to claim 1, wherein said micro-capsules have a diameter equal to or less than 10 micrometers.

21. The method according to claim 1, wherein said micro-capsules have a diameter equal to or less than 5 micrometers.

22. The method according to claim 1, wherein said micro- or nano-capsules have a diameter equal to or less than 100 nanometers.

23. A method comprising the steps of:

providing at least one adjuvant substance;

providing at least one non-ionic surface-active agent;

mixing said at least one adjuvant substance with said at least one non-ionic surface-active agent to form a mixture consisting of said at least one adjuvant substance and said at least one non-ionic surface-active agent;

providing an aqueous solution of a cationic surface-active agent;

mixing the mixture of said at least one adjuvant substance and said at least one non-ionic surface-active agent in said aqueous solution of said cationic surface-active agent to form thereby an aqueous nano- or micro-emulsion containing nano- or micro-droplet of at least one adjuvant substance encapsulated in a protective layer comprising said at least one non-ionic surface-active agent, the cationic surface-active agent co-acting with the at least one non-ionic surface-active agent in forming an envelope of said nano- or micro-droplets, the envelope being formed while mixing said mixture of said at least one adjuvant substance and said at least one non-ionic surface-active agent with said aqueous solution of said cationic surface-active agent, wherein the envelope is formed by the cationic agent and the at least one non-ionic surface-active agent, the cationic surface-active agent stabilizing the envelope containing said at least one adjuvant substance, the cationic surface-active agent being in contact with the at least one non-ionic surface-active agent prior to forming the envelope;

applying said nano- or micro-emulsion to a cellulose material to provide a nano- or micro-emulsion cellulose material; and evaporating water from said nano- or micro emulsion cellulose material to form nano- or micro-capsules anchored to the cellulose fibers to form a cellulose sheet material, said cellulose sheet material having a cellulose fiber-based structure and said cellulose sheet material comprising said at least one adjuvant substance for treatment of allergic rhinitis.

24. A method for producing a cellulose sheet material, the method comprising the steps of:

forming a mixture of the at least one adjuvant substance for the treatment of allergic rhinitis with at least one non-ionic surface-active agent;

mixing the mixture of the at least one non-ionic surface-active agent and the at least one adjuvant substance for the treatment of allergic rhinitis in an aqueous solution of a cationic surface-active agent forming thereby an aqueous nano- or micro-emulsion containing nano- or micro-droplet of the at least one adjuvant substance encapsulated in a protective layer comprising the least one non-ionic surface-active agent, the cationic surface-active agent co-acting with the at least one non-ionic surface-active agent in forming an envelope of said nano- or micro-droplets, wherein the envelope is formed by the cationic agent and the at least one non-ionic surface-active agent, the envelope being formed while mixing the mixture of the at least one non-ionic surface-active agent and the at least one adjuvant substance with the aqueous solution of the cationic surface-active agent, the cationic surface-active agent stabilizing the protective layer containing the at least one adjuvant substance, the cationic surface-active agent being in contact with the at least one non-ionic surface-active agent prior formation of the envelope;

applying said nano- or micro-emulsion to the cellulose material having a cellulose fiber-based structure; and evaporating water, leading to the formation of nano- or micro-capsules anchored to the fiber-based structure of the cellulose sheet material.

25. The method according to claim 24, wherein the mixture is formed in an absence of polymer and an organic solvent, wherein the envelope is formed in a manufacturing step which starts when no envelope exists.

* * * * *